US007210206B2

(12) United States Patent
Ferguson

(10) Patent No.: US 7,210,206 B2
(45) Date of Patent: May 1, 2007

(54) GEL-FORMING FABRIC COMPOSITE

(75) Inventor: Paul John Ferguson, Coventy (GB)

(73) Assignee: Convatec Limited (GB)

(*) Notice: Subject to any disclaimer, the term of this patent is extended or adjusted under 35 U.S.C. 154(b) by 470 days.

(21) Appl. No.: 10/490,813

(22) PCT Filed: Oct. 10, 2002

(86) PCT No.: PCT/GB02/04575

§ 371 (c)(1),
(2), (4) Date: Mar. 25, 2004

(87) PCT Pub. No.: WO03/033041

PCT Pub. Date: Apr. 24, 2003

(65) Prior Publication Data

US 2004/0244164 A1 Dec. 9, 2004

(30) Foreign Application Priority Data

Oct. 12, 2001 (GB) .................. 0124530.7

(51) Int. Cl.
*D04H 1/46* (2006.01)
(52) U.S. Cl. .......................... 28/107; 28/112
(58) Field of Classification Search .................. 28/107, 28/108–115, 103, 104, 105, 106; 442/402, 442/383, 387, 388, 389, 403, 394; 602/41–46, 602/48, 49; 604/304, 367, 368, 383; 424/445, 424/443, 446, 447, 449
See application file for complete search history.

(56) References Cited

U.S. PATENT DOCUMENTS

| 1,726,634 | A | * | 9/1929 | Smith | 428/85 |
|---|---|---|---|---|---|
| 4,562,110 | A | * | 12/1985 | Tong | 442/368 |
| 4,632,880 | A | | 12/1986 | Lapidus | 428/523 |
| 4,977,892 | A | * | 12/1990 | Ewall | 602/52 |
| 5,197,945 | A | * | 3/1993 | Cole et al. | 28/105 |
| 5,238,685 | A | * | 8/1993 | Wren | 424/445 |
| 5,256,477 | A | * | 10/1993 | Mahoney | 28/107 |
| 5,340,363 | A | * | 8/1994 | Fabo | 604/304 |
| 5,489,262 | A | | 2/1996 | Cartmell et al. | 602/57 |
| 5,674,524 | A | | 10/1997 | Scherr | 424/445 |
| 5,714,232 | A | * | 2/1998 | Fenton et al. | 428/171 |
| 6,077,526 | A | | 6/2000 | Scully et al. | 424/443 |

FOREIGN PATENT DOCUMENTS

| EP | 0578107 A1 | 1/1994 |
|---|---|---|
| GB | 990689 | 4/1965 |
| GB | 1394742 | 5/1975 |
| WO | WO 90/01954 A1 | 3/1990 |
| WO | WO 96/13282 A1 | 5/1996 |
| WO | WO 96/36304 A1 | 11/1996 |
| WO | WO 99/67456 A1 | 12/1999 |

OTHER PUBLICATIONS esp@cenet database, one page English abstract of EP 0578107, Jan. 1994.

* cited by examiner

*Primary Examiner*—A. Vanatta
(74) *Attorney, Agent, or Firm*—John M. Kilcoyne

(57) ABSTRACT

A method for the manufacture of a reinforced gel-forming fabric composite comprising a reinforcing layer and gel-forming fibre material is characterized in that the gel-forming fibre material in non-woven fabric form is needled into the reinforcing layer from one side so as to penetrate through the reinforcing layer and form a layer of gel-forming fibre material on both sides of the reinforcing layer. The resulting fabric finds use in a wound dressing.

15 Claims, No Drawings

GEL-FORMING FABRIC COMPOSITE

FIELD OF THE INVENTION

The present invention relates to an improved method for making a fabric composite comprising, gel-forming fibre material, in particular alginate fibre material.

It is known to produce fabrics from gel-forming fibres, in particular alginate fibres, more particularly either calcium alginate or sodium/calcium alginate. These fibres and the fabrics produced from them have the characteristic that when brought into contact with water containing certain ions, particularly sodium ions, they react to form a gel. Gel-forming fibres such as alginate fibres are, therefore, very useful in the production of wound dressings. Similarly, fabrics made from carboxymethyl cellulose fibres are gel-forming in the presence of water and are also useful for wound dressings.

BACKGROUND ART

U.S. Pat. No. 5,674,524 describes and claims an alginate dressing which is needle punched onto a non-alginate backing web so that fibres from the alginate layer penetrate into and are interlocked with the backing web. In the fabric described in that specification there is clearly a backing layer on one side of the product which is a non-alginate layer and an alginate dressing on the front side of the product. All of the description is concerned with the penetration of the alginate fibres into the backing layer to produce a continuous product. In column 5, lines 25 to 32, it is specified that a particular advantage of the alginate dressing containing a backing is the ease with which an adhesive strip can be placed on the backing and hold the alginate dressing in place. Because alginate becomes hydrocolloidal, i.e. gels, in an exudating wound the adhesive strip would become moist and easily disassociated from the alginate dressing should the alginate material have penetrated the backing. Thus, the US patent is clearly directed to a two-layer structure in which the backing does not have alginate on its exterior.

WO-A-99/67456 describes the formation of a three-layer structure for a fabric composite comprising two outer gel-forming fibre layers which sandwich a central core or reinforcing layer. The three-layer structure is produced by needling first and second webs of gel-forming fibre to a textile fibre scrim so as to produce a fabric with the gel-forming fibres on both sides. As described in Example 2 of WO-A-99/67456, the fabric composite can be made by laying up cross-laid, carded and needled webs of a gelling fibre such as carboxymethyl cellulose on either side of a spun-bonded fabric, typically a polypropylene fabric. The assembly is then needled together to produce the fabric.

GB-A-1,394,742 discloses surgical dressing material comprising a layer of knitted alginic material adhered to one side of a layer of flexible backing material by damping followed by drying.

WO-A-90/01954 discloses a wound dressing comprising a wound contact pad of a mixed salt alginate and a backing layer which may be bonded to the wound contact pad by adhesive.

U.S. Pat. No. 5,340,363 discloses a wound dressing comprising as wound-contacting surface a porous hydrophobic layer composed of an elastic net-like porous reinforcing component substantially completely encapsulated by a soft and elastic hydrophobic gel such as silicone gel whilst retaining the porosity of the net-like reinforcing component, so that the layer includes openings which permit wound exudate to pass through the hydrophobic layer to be absorbed in an outer absorbent layer attached to the hydrophobic layer.

U.S. Pat. No. 5,489,262 discloses a wound dressing containing a hydrogel material in a gel-like phase adhesively bonded to a support layer which is adhesively bonded to a backing layer.

WO-A-96/13282 discloses a wound dressing comprising a wound-contacting layer having a positive effect on the healing of the wound, for example an alginate layer, and a second layer of greater hydrophilicity than the first layer, for example an alginate or carboxymethyl cellulose layer.

DISCLOSURE OF THE INVENTION

We have now found that it is possible to provide what appears to be a three-layer structure, comprising a pair of gel-forming fibre layers sandwiching a central core or reinforcing layer, from just two layers of material. It has surprisingly been found that if a non-woven alginate or other gel-forming fabric, for example formed by non-woven carding and cross-folding, is needled onto a scrim central core or reinforcing layer it is possible for the non-woven alginate fabric to be needle punched completely through the scrim central core or reinforcing layer so that the non-woven alginate fibre material appears on both sides of the reinforcing layer and the reinforcing layer becomes buried within the structure. This gives the appearance of the scrim being centred and remaining virtually invisible on the face surfaces of the fabric composite. The scrim can be viewed from the edges of the composite but effectively cannot be seen from the faces.

It is particularly surprising that this can occur with alginate fibres as gel-forming fibres given that alginate fibres are weak fibres and they are punched completely through the centre scrim layer.

According to the present invention, therefore, a method for the manufacture of a reinforced gel-forming fabric composite comprising a reinforcing layer and gel-forming fibre material, is characterised in that the gel-forming fibre material in non-woven fabric form is needled into the reinforcing layer from one side so as to penetrate through the reinforcing layer and form a layer of gel-forming fibre material on both sides of the reinforcing layer.

The fabric composites made by the method of the invention are differentiated from those made from three layers as in WO-A-99/67456 by the fact that, because the gel-forming fibre material is on only a first side of the scrim reinforcing layer prior to needle punching, the two apparent layers in the finished product have a single origin rather than being initially separate.

The fabric composites are differentiated from known composites in which gel-forming fibre material is needled into the first side of a web of non-gel-forming fibre as in U.S. Pat. No. 5,674,524 by the fact that the gel-forming fibres extend through the web of non-gel-forming fibre to cover the opposite side of that web and form a layer of gel-forming fibre material over it on both sides.

The fabric composites find use as wound dressings, where they can form the wound contacting surface of the dressing.

The scrim central core or reinforcing layer may comprise any suitable woven, non-woven or knitted fabric. When the fabric composite is to be used as a wound dressing the scrim may contain an anti-microbial agent or be medicated, for example using an anaesthetic such as lidocaine hydrochloride.

In a preferred embodiment according to the invention when the fabric composite is to be used as a wound dressing, the scrim central core or reinforcing layer is sputtered or otherwise coated or impregnated with silver prior to needling the alginate through the scrim layer. Particularly in this embodiment, the scrim is preferably a cellulosic fibre layer such as lyocell or a synthetic fibre layer such as nylon, polyester or polyethylene.

The scrim confers on the gel-forming fabric an increased level of tensile strength that ensures one-piece removal of the fabric composite from the wound site when it is used as a wound dressing. This is difficult to achieve when gel-forming fibres are used, without reinforcement, particularly alginates, especially in bulky non-woven form, which is the form giving maximum softness, conformability and absorbency for wound dressings.

A number of benefits result from the invention. Firstly, one-piece removal of the fabric composite is ensured. Secondly, the strengthened fabric is particularly useful as a cavity dressing in the form of a tape, i.e. a narrow fabric, where the leaving behind of dressing material might go unnoticed or else the material left behind might be difficult to retrieve, at dressing changes. Thirdly, there is no contact between the scrim reinforcing layer and the wound whichever face of the fabric composite touches the wound, due to effect of the gel-forming layer. Finally, the fabric can be formed as a lightweight fabric because it is formed using a single gel-forming web only.

The fabric according to the invention can be manufactured by a single pass process through a single board needle loom, yet it gives the appearance of a structure manufactured by two passes, i.e. by needling from top and bottom. There is no detrimental effect on absorbency.

The webs which may be used to produce the alginate layers include calcium alginate or sodium/calcium (fast gel) alginate (basis weight 70–200 gm$^{-2}$). These are bonded to, for example, a lyocell woven gauze scrim (40 μm$^{-2}$) by passing through a single board needle loom, with the alginate web as the top layer and the scrim as the bottom layer. Needling through the alginate web into the scrim is preferably carried out using needles available from Foster Needles Limited, of Leicester, England, of the type 15×18×38×3RBA, F20 6-3B. The needle punch density is preferably in the range of 40–200 ncm$^{-2}$, with a penetration of 4–15 mm. Carboxymethyl cellulose may alternatively be used as gel-forming fibre.

The invention is further illustrated by the following Example.

EXAMPLE

A 50/50 sodium/calcium alginate was cut into 50 mm staple, opened through a Shirley Wheel opener, carded and crossfolded into a nonwoven web having a basis weight of 125 gm$^{-2}$ by the following method.

Fibre was fed through a Tathams Roller and Clearer card with five sets of workers—and strippers to form a card web at the doffer of 12 gm$^{-2}$. The card web was fed through an Interweb crosslapper to provide a 10-layer structure and compressed by the action of a weighted roller at the outlet to the crosslapper. Medical grade paper (which is a low linting and low shedding paper) was interleaved between the structure to ensure that on wind-up there was no delamination of adjacent layers.

The crossfolded fabric was unwound and fed into a Fehrer single board needleloom with a lattice feed and a stainless steel bed and stripper plate. The alginate structure was supported on a 40 gm$^{-2}$ woven lyocell fabric (plain weave) made from 80's cotton count lyocell by John Spencer Ltd (Burnley). Prior to the material being fed through the needleloom the medical grade paper was stripped away.

The operating parameters of the needleloom were as follows:

Needle type: 15×18×38×3RBA, F20 6-3B (Foster Needles)

Needle punch density: 80 ncm$^{-2}$ (uniform distribution with herring bone array)

Penetration: 10 mm

Needleboard stroke: 500 strokes per minute

Speed through loom: 2.5 m/min

Test Data:

The resultant needled composite fabric was tested with the following properties measured:

| Sample | Basis Weight (gm$^{-2}$) | Shrinkage (%) (i) | Absorbency (g/g) (ii) | Absorbency (g/100 cm$^{-2}$) | Wet Tensile Strength (N/cm) (iii) |
|---|---|---|---|---|---|
| Standard sodium/calcium alginate | 148 | 40.7 | 16.3 | 24.1 | 0.5 |
| Reinforced sodium/calcium alginate | 175 | 27.0 | 14.9 | 26.0 | 4.2 |

(i) Shrinkage is by area during the absorbency test:
(ii) The test method used was as set out in the British Pharmacopoeia-1993, addendum 1995, page 1706 in the section describing alginate dressings, the section headed Absorbency.
(iii) The test method used was as follows:
 1. The fabric was cut in the cross-direction into strips each measuring 10×2.5 cm.
 2. An Instron 1122 tensile machine was set up under the following conditions:—
  B-cell
  Yam jaws
  Test length 5 cm
  Cross head speed 10 cm/min
  Full scale load 2 Newtons
 3. The dry sample was placed into the jaws of the Instron machine.
 4. 2 ml of 0.9% sodium chloride was applied by syringe evenly onto the fabric.
 5. The sample was left for 1 minute.
 6. The chart recorder was checked to ensure that it was zeroed.

The invention claimed is:
1. A method for the manufacture of a reinforced gel-forming fabric composite having a reinforcing layer and gel-forming fibre material, comprising the step of needling the gel-forming fibre material in non-woven fabric form into the reinforcing layer from one side so as to penetrate through the reinforcing layer and form a layer of gel-forming fibre material on both sides of the reinforcing layer.

2. A method as claimed in claim 1, wherein the gel-forming fibre is alginate fibre.

3. A method as claimed in claim 2, wherein the alginate is a calcium alginate or sodium/calcium alginate.

4. A method according to claim 3, wherein the gel-forming fibre material is formed by non-woven carding and crossfolding of gel-forming fibre.

5. A method according to claim 4, wherein the gel-forming fibre material is needled at a needle punch density of from 40 to 200 ncm$^{-2}$.

6. A method according to claim 5, wherein the reinforced fabric is manufactured by a single pass through a single-board needle loom.

7. A method according to claim 6, wherein the reinforcing layer is selected from a group consisting of a woven cellulosic fibre layer, a non-woven cellulosic fibre layer, a knitted cellulosic fibre layer, and a synthetic fibre layer.

8. A method according to claim 7, wherein the reinforcing layer is selected from a group consisting of a lyocell fibre layer, a nylon fibre layer, a polyester fibre layer, and a polyethylene fibre layer.

9. A method according to claim 8, wherein the reinforcing layer is sputtered, coated or impregnated with silver prior to the gel-forming fibre being needled into and through it.

10. A method according to claim 1, wherein the gel-forming fibre material is formed by non-woven carding and crossfolding of gel-forming fibre.

11. A method according to claim 1, wherein the gel-forming fibre material is needled at a needle punch density of from 40 to 200 ncm$^{-2}$.

12. A method according to claim 1, wherein the reinforced fabric is manufactured by a single pass through a single-board needle loom.

13. A method according to claim 1, wherein the reinforcing layer is selected from a group consisting of a woven cellulosic fibre layer, a non-woven cellulosic fibre layer, a knitted cellulosic fibre layer, and a synthetic fibre layer.

14. A method according to claim 13, wherein the reinforcing layer is selected from a group consisting of a lyocell fibre layer, a nylon fibre layer, a polyester fibre layer, and a polyethylene fibre layer.

15. A method according to claim 1, wherein the reinforcing layer is sputtered, coated or impregnated with silver prior to the gel-forming fibre being needled into and through it.

* * * * *

UNITED STATES PATENT AND TRADEMARK OFFICE
CERTIFICATE OF CORRECTION

PATENT NO. : 7,210,206 B2 Page 1 of 1
APPLICATION NO. : 10/490813
DATED : May 1, 2007
INVENTOR(S) : Paul John Ferguson It is certified that error appears in the above-identified patent and that said Letters Patent is hereby corrected as shown below:

Column 3, line 47 - change "(40 um$^{-2}$)" to --(40 gm$^{-2}$)--

Signed and Sealed this

Twelfth Day of June, 2007

JON W. DUDAS
*Director of the United States Patent and Trademark Office*